United States Patent [19]
Oppe et al.

[11] Patent Number: 5,471,820
[45] Date of Patent: Dec. 5, 1995

[54] METHOD OF AND APPARATUS FOR WRAPPING TAMPONS

[75] Inventors: Hans-Joachim Oppe, Midlothian, Va.; Alfred Hinzmann, Sarasota, Fla.; Peter M. Preisner, Quinton, Va.

[73] Assignee: Hauni Richmond, Inc., Richmond, Va.

[21] Appl. No.: 335,660

[22] Filed: Nov. 8, 1994

[51] Int. Cl.⁶ .................. B65B 5/06; B65B 9/06; B65B 9/10; B65B 51/14
[52] U.S. Cl. .................. 53/449; 53/465; 53/469; 53/474; 53/479; 53/173; 53/547; 53/550; 53/234; 53/236; 53/371.2
[58] Field of Search .............. 53/413, 449, 450, 53/451, 464, 465, 466, 477, 479, 234, 236, 550, 551, 547, 371.2, 371.6, 372.5, 372.8, 469, 474, 173

[56] References Cited

U.S. PATENT DOCUMENTS

| | | | |
|---|---|---|---|
| 2,371,874 | 3/1945 | Chapman et al. | 53/372.8 X |
| 2,383,664 | 8/1945 | Malhiot | 53/372.8 X |
| 3,001,351 | 9/1961 | Brook et al. | 53/547 X |
| 3,296,772 | 1/1967 | Barker | 53/372.8 |
| 3,382,644 | 5/1968 | Vogt | 53/479 X |
| 3,432,986 | 3/1969 | Schneider et al. | 53/547 |
| 3,452,505 | 7/1969 | Hoag | 53/479 X |
| 3,807,132 | 4/1974 | Kamiya | 53/372.8 X |
| 3,982,374 | 9/1976 | Schaefer | 53/479 X |
| 4,845,922 | 7/1989 | Sweere | 53/451 X |
| 5,024,046 | 6/1991 | Spatafora et al. | 53/466 |

*Primary Examiner*—Horace M. Culver
*Attorney, Agent, or Firm*—Darby & Darby

[57] ABSTRACT

Digital tampons carrying strings are surrounded in tubular envelopes while being confined in and advancing with upright cylindrical carriers. The envelopes are formed around the carriers so that their lower ends extend beyond the lower ends of the respective carriers. The lower ends of successive envelopes are closed by providing them with at least partially overlapping panels. Prior to being separated from the respective carriers, the closed ends of the envelopes are deformed by heated profiled tools which provide the outer sides of the closed ends with centrally located recesses surrounded by smooth ring-shaped portions. The strings are automatically curled along the marginal portions at the upper sides of the respective closed ends in response to downward movement of the tampons in their carriers not later than in the course of the deforming step. The tampons are thereupon advanced downwardly so that they strip the tubular envelopes off the respective carriers, and the upper ends of the envelopes are closed or closed and sealed during advancement beyond the stripping station.

26 Claims, 2 Drawing Sheets

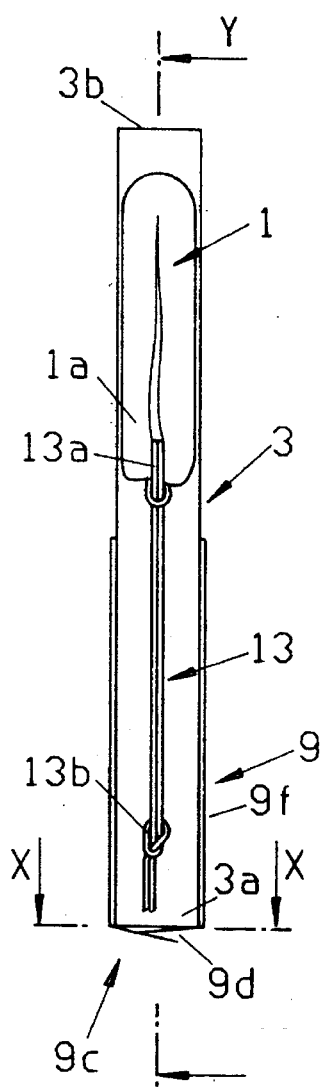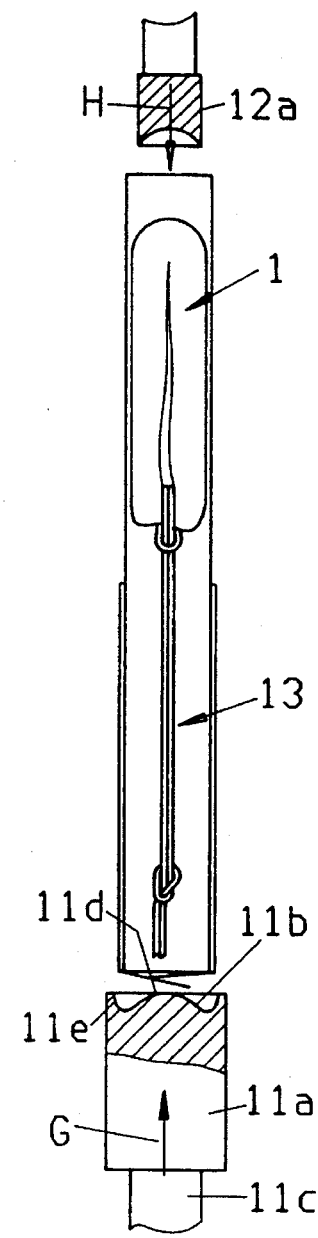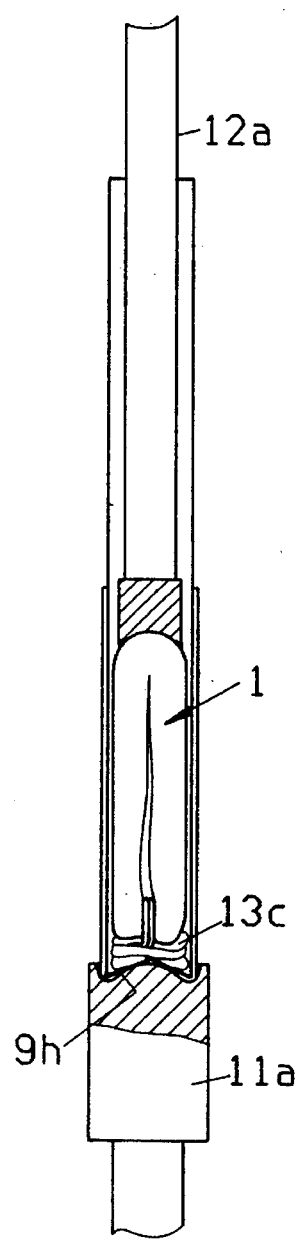
Fig.2  Fig.4  Fig.5
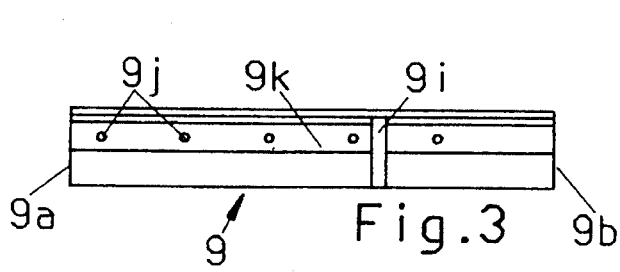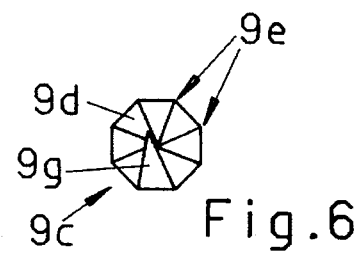
Fig.3  Fig.6

METHOD OF AND APPARATUS FOR WRAPPING TAMPONS

BACKGROUND OF THE INVENTION

The present invention relates to articles of feminine hygiene known as tampons, and more particularly to improvements in so-called digital tampons which are insertable directly by hand and, as a rule, are provided with strings serving to facilitate manual extraction of tampons from body cavities.

A digital tampon normally resembles an elongated bullet-shaped cylinder having a rounded leading end and a trailing end or another part attached to one end of a string the other end of which is accessible at the exterior of the inlet to the body cavity which receives the tampon. Each tampon is confined in a tubular envelope which is or which can be made of a light-transmitting material and is closed at both ends. An intermediate portion of the envelope is or can be provided with a tear strip which facilitates access to the tampon preparatory to introduction into a body cavity. The string is stored in the envelope in folded condition adjacent the trailing end of the tampon.

Attempts to facilitate predictable folding of strings at the trailing ends of the tampons prior to closing of both ends of the respective tubular envelopes include the introduction of tampons and of the respective strings into tubular carriers and circulation of air in the carriers for the purpose of influencing the folding of the strings, i.e., the ultimate shape and positioning of the string within the confines of a closed tubular envelope at the trailing end of the respective tampon. The utilization of currents of air contributes significantly to the complexity and cost of heretofore known apparatus which are designed to confine tampons and their strings in tubular envelopes. Moreover, the utilization of air currents does not ensure predictable folding of the strings; as a rule, the folded portions of a string extend randomly in part across and in part along short arcuate paths at the trailing ends of the respective tampons.

Another drawback of heretofore known methods of and apparatus for confining digital tampons in tubular envelopes is that the configuration of the closed ends of tubular envelopes at the trailing ends of the confined tampons varies from tampon to tampon. Such closing is effected by devices which fold the respective still open ends of the tubes not unlike the flaps of envelopes so that the thus obtained closed ends include a plurality of partially overlapping panels intended to be disposed in planes which are normal to the longitudinal axes of the respective tampons. Neighboring panels define relatively sharp corner portions or "ears" which are apt to scratch the hand of the person desiring to remove the tubular envelope from a confined tampon and its string.

Still another drawback of heretofore known methods of and apparatus for confining digital tampons in tubular envelopes is that the closed ends of the envelopes at the trailing ends of the confined tampons are not adequately sealed. As a rule, such sealing is effected by advancing the closed ends of envelopes at the trailing ends of the confined tampons along a heated surface which is supposed to establish a bond between the overlapping or partially overlapping panels at the respective closed ends of the envelopes. Such treatment does not ensure reliable bonding of the partially or fully overlapping panels to each other. In addition, the advancement of tubular envelopes along a heated surface is likely to intensify the formation of the aforediscussed undesirable corner portions or "ears".

An additional drawback of conventional methods of and apparatus for confining digital tampons in tubular envelopes is that the desirable recesses at the trailing ends of the tampons are likely to disappear or that their depth is reduced and/or that their shape is altered during storage of confined tampons. Such recesses are desirable for convenient application of the tip of an index finger or another finger during introduction of an unsealed tampon into a body cavity. The aforediscussed advancement of closed ends of tubular envelopes adjacent the trailing ends of confined tampons is likely to contribute to a reduction of the depth of recesses in the trailing ends of the tampons. Furthermore, the condensed material of a confined tampon tends to expand in the interior of its envelope. A finished envelope does not or is not likely to yield in a radial direction; however, it does not interfere with an expansion of the tampon in a direction to reduce the depth of the recess in its trailing end.

Last but not least, tampons which are confined in tubular envelopes exhibiting some or all of the aforediscussed drawbacks and/or defects cannot be readily collated and introduced into cartons or other receptacles for arrays consisting of selected numbers of confined tampons. In addition, the lack of uniformity of closed ends of tubular envelopes adjacent the trailing ends of the confined tampons detracts from the appearance of such products.

OBJECTS OF THE INVENTION

An object of the invention is to provide a novel and improved method of confining digital tampons in tubular envelopes (hereinafter called tubes for short).

Another object of the invention is to provide a method which renders it possible to impart a desired configuration to the trailing ends of confined tampons, to the strings which are affixed to the trailing ends of the tampons as well as to the adjacent closed ends of the tubes.

A further object of the invention is to provide a novel and improved method of shaping the ends of tubes adjacent the trailing ends of the confined tampons.

An additional object of the invention is to provide a novel and improved method of eliminating, or at least reducing the prominence, of corner portions or "ears" at the closed ends of tubes adjacent the trailing ends of confined tampons.

Still another object of the invention is to provide a method which renders it possible to close the ends of tubes in a highly predictable manner so that the dimensions as well as the configuration of each of a short or long series of successively closed and sealed tubes match a desirable optimum size and/or shape.

A further object of the invention is to provide a method which renders it possible to select the configuration as well as the dimensions of each of a short or long series of successively confined tampons in such a way that the confined tampons can be readily collated and packaged in a simple and time saving manner.

Another object of the invention is to provide novel and improved combinations of digital tampons, strings and tubes which are obtained in accordance with the above outlined method.

An additional object of the invention is to provide a novel and improved mode of predictably collapsing or folding strings which are connected with the trailing ends of digital tampons.

Still another object of the invention is to provide a method of imparting to the trailing ends of confined tampons an optimum configuration as a consequence of making and closing the tubes for confinement of the tampons.

A further object of the invention is to provide a method which renders it possible to simultaneously influence the making, closing and sealing of tubes, predictable collapsing or folding of the strings, and predictable shaping of the trailing ends of digital tampons.

Another object of the invention is to provide a novel and improved apparatus for the practice of the above outlined method.

An additional object of the invention is to provide the apparatus with novel and improved means for sealing and shaping those ends of the tubes which are adjacent the trailing ends of the confined tampons.

Still another object of the invention is to provide the apparatus with novel and improved means for influencing the configuration of the trailing ends of confined digital tampons simultaneously with predictable and reliable sealing of the adjacent end portions of the respective tubes.

A further object of the invention is to provide a simple, compact and reliable apparatus for the mass production of confined digital tampons at a rate greatly exceeding the outputs of heretofore known apparatus.

Another object of the invention is to provide the apparatus with novel and improved means for eliminating or at least reducing the dimensions of the aforediscussed corner portions or "ears" at the closed ends of tubes adjacent the trailing ends of the confined tampons.

An additional object of the invention is to provide the above outlined apparatus with means for ensuring predictable and optimal folding or collapsing of strings which are or which can be attached to the trailing ends of digital tampons.

Still another object of the invention is to provide an apparatus which can turn out confined digital tampons of such size and shape that the tampons can be readily collated and packaged and that the tampons can be readily manipulated by ultimate users for the purpose of removing their tubular envelopes as well as for the purpose of inserting them into body cavities.

SUMMARY OF THE INVENTION

One feature of the present invention resides in the provision of a method of confining an elongated substantially cylindrical tampon. The method comprises the steps of introducing the tampon into a tubular carrier, surrounding at least a portion of the carrier by a blank of flexible sheet material and converting the blank into a tube having a first open end remote from and a second open end extending beyond an open end of the carrier, closing the second end of the tube including providing the second end with a plurality of at least partially overlapping panels which are disposed at least close to a plane at least substantially normal to a longitudinal axis of the carrier and which, as a rule, define at least one corner portion projecting substantially radially of and away from the axis of the carrier and beyond an external surface of a portion of the tube adjacent the aforementioned plane, and deforming the closed end of the tube including at least reducing the extent to which the at least one corner portion projects beyond the external surface.

The sheet material of the blank is preferably deformable (or more readily deformable) in response to the application of heat, and the deforming step can include heating the closed end of the tube. For example, the material of the blank (i.e., the material of the tube) can be selected from the group including cellophane and polypropylene.

The deforming step can include providing the outer surface of the closed end of the tube with a recess, preferably with a recess the making of which involves the making of a similar recess in one end of the confined tampon.

The method further comprises the step of expelling the tampon through the open end of the carrier with attendant separation of the tube from the carrier (namely stripping of the tube off the carrier) as a result of impingement of the tampon upon the closed and deformed end of the tube. Such expelling step is normally followed by the step of closing the first end of the tube, e.g., in a manner similar to closing the upper ends of cardboard containers for milk or other liquids. The expelling step can include advancing in the carrier a pusher against the tampon and in a direction to move the tampon through and beyond the open end of the carrier.

In accordance with a presently preferred embodiment, the method further comprises the step of advancing the carrier substantially at right angles to its longitudinal axis in the course of at least one of the introducing, surrounding, closing, deforming and sealing steps.

The introducing step can include positioning the tampon in the carrier at a location at least slightly spaced apart from the open end of the carrier, and such method preferably further includes the step of shifting the tampon relative to the carrier toward the closed end of the tube not later than in the course of the deforming step.

As a rule, a tampon of the type to be confined in accordance with the above outlined method is provided with an elongated string having a first end which is carried by the tampon and a second end which is remote from the trailing end of the tampon when the string is under tension. The method of confining tampons which are provided with strings preferably further comprises the step of maintaining the carrier in an at least substantially upright position so that the open end of the carrier is located below the other end. The introducing step then includes causing the string and thereupon the tampon to enter the carrier through the other end of the carrier so that the string depends from the tampon under the action of gravity, and such method further comprises the step of shifting the tampon in the carrier toward the closed end of the tube prior to the deforming step whereby the string curls above and along the closed end of the tube adjacent the open end of the carrier. The deforming step of such method preferably includes displacing a substantially central portion of the closed end of the tube toward the trailing end of the tampon in the carrier so that the displaced central portion of the closed end is at least partially surrounded by the coiled string.

If the elimination (or at least a reduction of the prominence) of the aforementioned edge portion or portions is not overly important to the maker of confined tampons, the deforming step can include only the provision of a recess in the exposed outer surface of the closed end of the tube. However, such deforming step can also include imparting an at least substantially circular shape to a portion of the closed end which surrounds the recess. This automatically entails the elimination (or at least a considerable reduction of the prominence) of the aforediscussed corner portion or portions.

Another feature of the invention resides in the provision of an apparatus for confining elongated substantially cylindrical tampons. The apparatus comprises means (e.g., an endless chain) for advancing a series of successive open-ended tubular carriers along a predetermined path, means for introducing tampons into successive carriers in a first portion of the path, means for draping blanks of flexible sheet material around successive carriers in a second portion of the path including means for converting the blanks into open-ended tubes each having a first open end remote from and a second open end extending beyond an open end of the respective carrier, means for closing the second open ends of tubes surrounding the respective carriers in a third portion of the path including means for providing each closed end with a plurality of at least partially overlapping panels each of which is disposed at least close to a plane at least substantially normal to a longitudinal axis of the respective carrier and which define at least one corner portion projecting substantially radially of and away from the respective axis and beyond an external surface of a portion of the tube adjacent the aforementioned plane, and means for deforming the closed ends of tubes surrounding successive carriers in a fourth portion of the path including means for at least reducing the extent to which the corner portions of closed ends of the tubes surrounding the respective carriers project beyond the corresponding external surfaces.

The apparatus further comprises means for expelling the tampons from successive carriers in a fifth portion of the path including means for displacing the tampons through and beyond the open ends of the respective carriers so that the tampons strip the corresponding tubes off their carriers.

If the blanks consist of a sheet material which is deformable (or more readily deformable) in response to the application of heat, the deforming means can include profiled heating means serving to contact the closed ends of tubes surrounding the respective carriers in the fourth portion of the path. The profiled heating means can include at least one tool having a surface confronting the closed end of a tube in the fourth portion of the path, and means for effecting a movement of the at least one tool toward a tube and/or of a tube toward the at least one tool in the fourth portion of the path in order to effect an exchange of heat between the surface of the at least one tool and the confronting closed end of the tube. The surface of the at least one tool can be provided with a protuberance (e.g., a substantially conical or hemispherical protuberance) which is engageable with a central portion of the closed end of a tube in the fourth portion of the path, or with a protuberance and a recess which surrounds the protuberance and is bounded by a surface serving to eliminate or to at least reduce the prominency or size of the aforementioned edge portion or edge portions defined by the panels of the closed ends of the tubes.

If the apparatus is utilized to confine digital tampons of the type provided with elongated strings or strands each having a first end carried by the respective tampon and a second end which is remote from the trailing end of the tampon when the string is subjected to a tensional stress, the advancing means preferably includes means for maintaining each carrier in an at least substantially upright position so that the open end of each carrier is located below the tampon in the respective carrier. The introducing means of such apparatus preferably includes means for causing each string and thereupon the corresponding tampon to enter through an open upper end of the respective carrier so that the string depends from the corresponding tampon by gravity, and such apparatus preferably further comprises means for shifting the tampons in the respective carriers downwardly toward the closed ends of the respective tubes not later than in the fourth portion of the path whereby the strings automatically curl along the upper sides of closed ends of the respective tubes adjacent the open lower ends of the respective carriers. The deforming means can include means for displacing a substantially central portion of the closed end of a tube in the fourth portion of the path toward the trailing end of the respective tampon so that the displaced substantially central portion is at least partially surrounded by the respective coiled string. The aforementioned shifting means can form part of the aforementioned expelling means or vice versa.

The advancing means can include means for moving successive carriers of the series sideways in a predetermined direction, and the first portion of the path is preferably located upstream of the second portion of the path, as seen in the predetermined direction.

The expelling means can be designed to expel the tampons from the respective carriers of the series from the fifth portion of the predetermined path into a second path, and such apparatus preferably further comprises means for closing the open first ends of the tubes in the second path.

If the closing of the second ends of the tubes does not result in the formation of pronounced corner portions or if the elimination (or at least a pronounced reduction of the prominence or size) of the corner portions is not important to the maker of the confined tampons, the deforming means can merely include or constitute means for providing the outer surface of each closed end with a recess. However, it is presently preferred to employ deforming means which further includes means for imparting a substantially circular shape to that portion of each closed end which surrounds the respective recess. This entails an automatic elimination or at least a pronounced reduction of the size of the corner portions.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of several presently preferred specific embodiments with reference to the accompanying drawings.

BRIEF DESCRIPTION OF THE DRAWINGS

FIG. 2 is a schematic axial sectional view of a tubular carrier, of a tampon and a string in the interior of the carrier, and of a tube the lower end of which is closed preparatory to deformation in response to the application of pressure and/or heat;

FIG. 3 is an elevational view of a tube prior to closing of its lower end;

FIG. 4 illustrates the structure of FIG. 2, a plunger or pusher which serves to shift a tampon in the interior of its carrier, and a tool which forms part of the means for deforming the closed lower end of the tube;

FIG. 5 is a view similar to that of FIG. 4 but showing the plunger or pusher in an intermediate position and the tool in the process of deforming the closed end of the adjacent tube; and FIG. 6 is a bottom plan view of the closed end of a tube prior to deformation by the tool of FIGS. 4 and 5.

Figure 1:
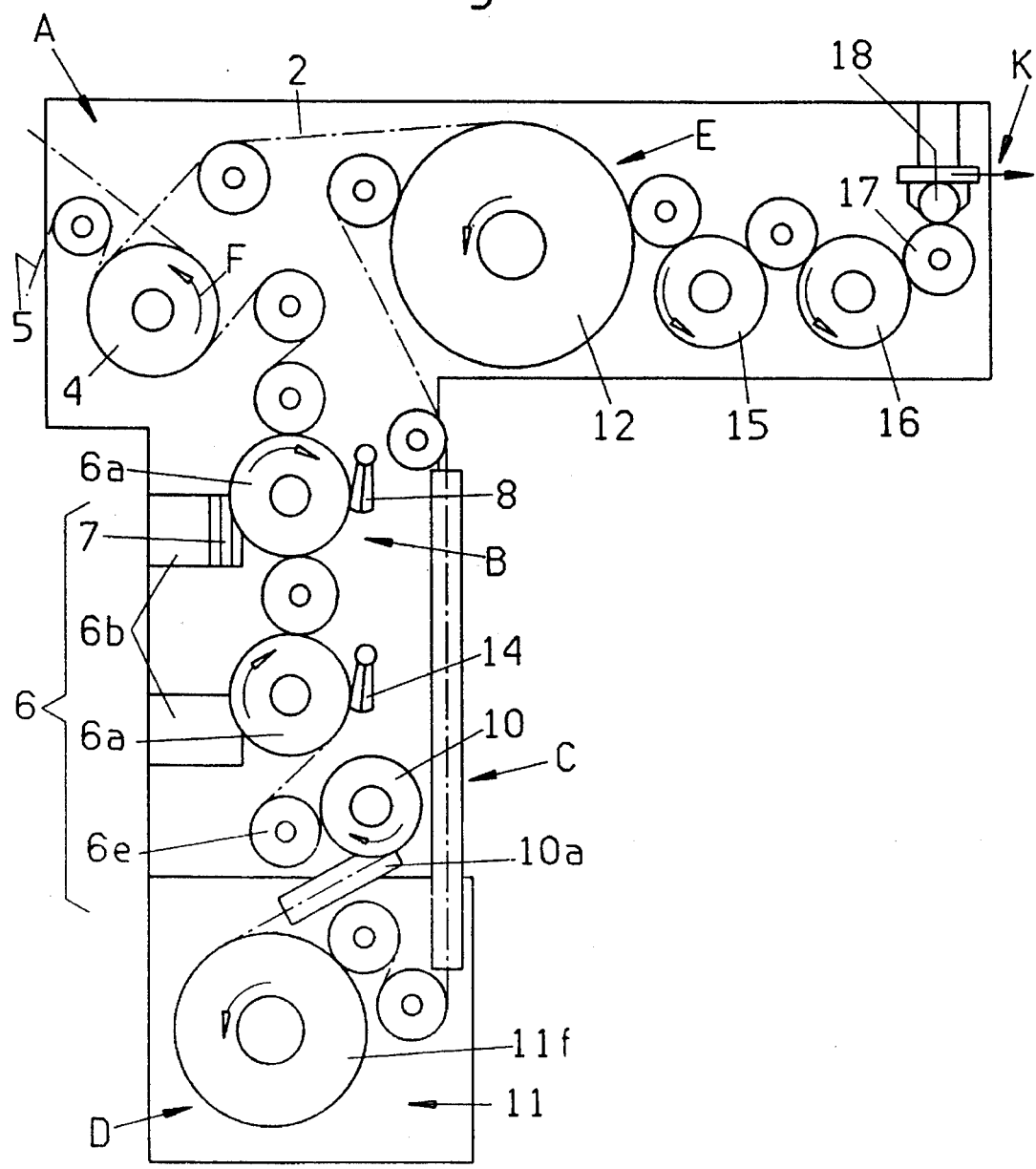
FIG. 1 is a schematic plan view of an apparatus which embodies one form of the instant invention.

DESCRIPTION OF PREFERRED
EMBODIMENTS

Referring first to FIG. 1, there are shown all relevant parts of an apparatus which embodies one form of the present invention and is utilized to confine elongated substantially cylindrical (bullet-shaped) digital tampons 1 (FIGS. 2, 4 and 5) in tubes 9 (FIGS. 2 to 6) which can be made of a light-transmitting material such as polypropylene, cellophane or other suitable sheet material. The tube 9 of FIG. 3 is provided with a tear strip 9i which enables the user to gain access to the tampon 1 and to an elongated string 13 (FIGS. 2, 4 and 5) one end (13a) of which is carried by (e.g., affixed to the adjacent trailing end 1a of) the respective tampon 1 and the other end (13b) of which is remote from the tampon when the string 13 is tensioned by gravity (as shown in FIGS. 2 and 4) or when the end 13b is pulled by the fingers of a person desiring to extract the tampon 1 from a body cavity.

Each tube 9 constitutes a converted blank 7 (FIG. 1) which was severed from a web (coming from a bobbin) and is draped around one of a series of successive elongated tubular (preferably cylindrical) carriers 3 which are advanced along an elongated path in the direction of arrow F by an endless chain or belt 2 in such positions that the central longitudinal axes Y—Y of the carriers 3 are at least substantially vertical, that the carriers 3 advanced by the belt or chain 2 are equidistant from each other (as seen in the direction of the arrow F), and that the open upper ends 3b of successive carriers are accessible at a first portion A of their endless path for introduction of discrete digital tampons 1 each of which is already connected with a string 13. The means for introducing discrete digital tampons 1 into successive carriers 3 on the belt or chain 2 includes an endless flexible belt or chain 5 which delivers a series of suitably spaced apart tampons (with strings 13 already depending from their trailing ends 1a) from a so-called knotting drum to the portion A of the path for the carriers 3. The belt or chain 5 also transports a series of carriers (not specifically shown) in the form of upright cylinders or the like each of which contains a tampon 1 and a string 13. The transfer of tampons 1 and the respective strings 13 from the carriers on the belt or chain 5 into successive empty carriers 3 on the belt or chain 2 takes place during advancement of the carriers 3 and the carriers on the belt or chain 5 around the periphery of a common transfer drum 4 which also forms part of means for introducing tampons 1 and strings 13 into successive empty carriers 3. The exact construction of the drum 4, of the belt or chain 5 and of the means for transferring tampons and strings from the carriers of the belt or chain 5 into the carriers 3 on the advancing means 2 is known in the art of making digital tampons and, therefore, such details are not shown in FIG. 1. It suffices to say that each carrier 3 which advances in the direction of the arrow F beyond the transfer drum 5 of the introducing means 4, 5 contains an upright tampon 1 and a string 13 having its upper end 13a affixed e.g. to the trailing (lower) end 1a of the tampon and its lower end 13b spaced apart from the trailing end 1a. Such string assumes the position shown in FIGS. 2 and 4 under the action of gravity.

Successive loaded or filled carriers 3 which advance beyond the transfer drum 5 enter a second portion (B) of the path for advancement of the tampons 1 with the belt or chain 2. The path portion B accommodates a unit (denoted by the reference character 6) which serves to sever successive blanks 7 from the leader of the running web and to drape successively severed blanks 7 around the oncoming successive carriers 3. A finished tube 9 is shown in FIG. 3. As already mentioned above, such tube is or can be provided with a tear strip 9i (tear strips are preferably provided on the running web or webs which are converted into successive blanks 7 consisting of cellophane or any other suitable sheet material). FIG. 1 merely shows two so-called metering or cutting devices 6b, two forming drums 6a and two so-called side tagging devices 8, 14. Successive blanks 7 are converted into tubes 9 during advancement of the respective carriers 3 along the first or upper forming drum 6a of the unit 6 (as viewed in FIG. 1), and the side tagging device 8 provides the overlapping marginal portions of successive open-ended tubes 9 with longitudinally spaced apart bonds 9j (which can be said to constitute spot welds) to ensure that the originally substantially trough-shaped partially deformed blanks 7 cannot open up (i.e., reassume a substantially trough-shaped configuration) on their way (with the respective carriers 3) from the first or upper transfer drum 6a toward the lower or second transfer drum 6a of the unit 6 shown in FIG. 1. The tagging device 14 provides the marginal portions of successive open-ended tubes 9 with longitudinally extending axially parallel seams 9k (FIG. 3) during advancement of such tubes with the carriers 3 travelling along the periphery of the second or lower forming drum 6a of the unit 6 shown in FIG. 1. The tagging devices 8 and 14 are or can be heated if the sheet material of the blanks 7 and tubes 9 is such that overlapping portions of the tubes 9 can be readily bonded to each other in response to the application of heat.

In addition to or in lieu of the second side tagging device 14, the unit 6 can comprise a so-called side sealing drum 6e which follows the second or lower transfer drum 6a and provides the overlapping marginal portions of successive tubes 9 with axially parallel seams 9k each of which extends or can extend all the way from the open end 9a to the open end 9b of the respective envelope or tube 9.

The side sealing drum 6e of the unit 6 shown in FIG. 1 is followed by means for closing the open lower ends 9b of successive tubes 9 in a plane (shown in FIG. 2 as a horizontal or substantially horizontal plane X—X) which is at least substantially perpendicular to the longitudinal axes Y—Y of the continuously advancing carriers 3. The closing means includes a so-called bottom folding drum 10 and a bottom ironing section 10a which follows the drum 10 and is located in a third portion C of the path for advancement of tampons 1 with the carriers 3.

A closed end 9b of a tube 9 is shown (at 9c) in each of FIGS. 2 and 4–6. Such closed end 9c includes a plurality of at least partially overlapping panels 9d which define one or more relatively sharp corner portions or "ears" 9e (FIG. 6) which, in the absence of any undertakings to the contrary, would detract from the appearance of the wrapped and sealed digital tampons and would even be likely to scratch the hand or hands of a user desiring to gain access to the tampon 1 and the corresponding string 13. Such user must at least partially remove the tear strip 9i of the respective closed and sealed tube 9. In fact, the action of the bottom ironing section 10a is likely to increase the pronouncedness or prominence of the corner portion or portions 9e, i.e., such corner portion or portions are even more likely to extend radially of the axes Y—Y of the respective carriers 3 and beyond the external surfaces 9f (FIG. 2) of those cylindrical or substantially cylindrical portions of the tubes 9 which are immediately adjacent the closed ends 9c.

In accordance with a feature of the invention, the bottom ironing section 10a can be replaced by or is used jointly with novel and improved means 11 for deforming the closed bottom ends 9c of successive tubes 9 while such tubes advance along a fourth portion D of the path for tampons 1 with the respective carriers 3. The sealing means 11 comprises a drum 11f which carries a set of equidistant vertically movable combined heating and deforming tools 11a (FIGS.

4 and 5) each of which is located below and is in axial alignment with one of the carriers 3 advancing with their chain or belt 2 along the periphery of the drum 11f. Each tool 11a has a profiled surface 11b provided with a centrally located upwardly extending protuberance 11d and an annular recess 11e surrounding the respective protuberance 11d. The means for effecting relative axial movements between the carriers 3 and the respective tools 11a includes vertical shafts 11c which support the tools 11a and are moved up and down during sidewise movement with and along the periphery of the combined bottom sealing and deforming or contouring drum 11f. For example, the tools 11a can be raised (arrow G in FIG. 4) and lowered by being provided with followers extending into the groove of a suitable cam installed beneath the path for the shafts 11c for the tools 11a. Such followers are or can be provided on the shafts 11c.

The drum 11f of the deforming means 11 further carries a set of pushers 12a (FIGS. 4 and 5) which serve as a means for shifting the tampons 1 in the respective carriers 3 in a downward direction (arrow H in FIG. 4) in order to effect automatic coiling of the strings 13 along the marginal portions of the upper sides of the closed ends 9c of the respective tubes 9 (compare FIGS. 4 and 5). Furthermore, the pushers 12a serve as a means for maintaining the respective tampons 1 in predetermined positions relative to the corresponding carriers 3, namely at selected distances from the open lower ends 3a and the upper ends 3b of such carriers (see FIG. 5). This ensures that the surfaces 11b of the respective heated tools 11a can influence the configuration of the respective closed ends 9c as well as the configuration of the undersides of trailing ends 1a of the respective tampons 1.

The protuberances 11d provide the undersides of the adjacent closed ends 9c with substantially conical recesses 9h (FIG. 5) in that they engage and lift the central portions 9g (FIG. 6) of the closed ends 9c. The height of the protuberances 11d is preferably selected in such a way that they lift the central portions 9g of the respective closed ends 9c into the spaces within the convolutions of collapsed strings 13c in the respective tubes 9. This can be readily seen in FIG. 5. Thus, the protuberances 11d not only provide the undersides of the adjacent closed ends 9c with recesses 9h (FIG. 5) but they also provide the undersides of trailing ends 1a of the tampons 1 with recesses resembling the recesses 9h in order to provide room for partial insertion of an index finger or any other finger which is utilized to introduce an unwrapped tampon 1 into a body cavity. If the trailing ends 1a of tampons 1 are provided with recesses prior to introduction into the respective carriers 3, the protuberances 11d of the tools 11a ensure that the desired depth of such recesses is reestablished during advancement of the respective carriers 3 along the periphery of the drum 11f in the event that the introduction of tampons into the carriers resulted in a reduction of the depth or in total elimination of recesses in the trailing ends of tampons advancing with the belt or chain 5.

The recesses 11e which are provided in the profiled surfaces 11b of the tools 11a and surround the bases of the respective substantially conical or hemispherical protuberances 11d serve to receive the lower open ends 3a of the adjacent carriers 3 as a result of lifting of the tools 11a toward the adjacent closed ends 9c of the tubes 9 (arrow G in FIG. 4). The lower ends 3a of the carriers 3 then cooperate with those portions of the surfaces 11b which surround the recesses 11e to ensure the elimination (or at least a pronounced reduction of the prominence) of corner portions 9e (if any) defined by the at least partially overlapping panels 9d forming the closed lower ends 9c. Thus, the corner portions or "ears" 9e no longer project radially outwardly beyond the external surfaces 9f of those portions of the tubes 9 which are immediately adjacent the closed ends 9c.

The pushers 12a can serve to merely shift the tampons 1 in the respective carriers 3 by being caused to descend from the positions corresponding to that of the pusher 12a shown in FIG. 4 to those corresponding to the position of the pusher 12a in FIG. 5. In addition, the pushers 12a can also serve as a means for ejecting or expelling tampons 1 from the respective carriers 3 if the expulsion of tampons from their carriers takes place while the carriers are in the process of advancing along the periphery of the bottom sealing and contouring drum 11f. As a pusher 12a advances downwardly and beyond the position shown in FIG. 5, the trailing end 1a of the tampon 1 pushes the closed and sealed end 9c of the tube 9 to share the downward movement of the pusher 12a so that the tampon strips the tube 9 off the carrier. Of course, the tool 11a must be lowered (in a direction counter to that indicated by the arrow G) in order to provide room for separation of the tube 9 from the corresponding carrier 3.

FIG. 1 shows that the separation of tubes 9 from their carriers 3 need not take place at the periphery of the drum 11f. Instead, the carriers 3, the tubes 9 surrounding the lower portions of such carriers and the tampons 1 and coiled strings 13a in such carriers are advanced along an elongated portion of the path for the carriers 3, namely a portion extending from the portion D toward a transfer drum 12 forming part of the means for expelling the tampons 1 from their carriers 3 in a fifth portion E of the path for the tampons 1. The drum 12 is or can be provided with a set of pushers 12a or similar pushers which are moved downwardly beyond the positions corresponding to that of the pusher 12a shown in FIG. 5 so that the tampons 1 are expelled from their carriers 3 and strip the corresponding tubes 9 off such carriers. At such time, the upper ends 9a of the tubes 9 are still open. The pushers 12a have concave undersides which are complementary to the exposed surfaces of the tips or leading ends of the tampons.

Freshly emptied carriers 3 continue to advance with the belt or chain 2 from the transfer drum 12 of the expelling means to the transfer drum 4 where they receive tampons 1 supplied by the endless belt or chain 5.

The tampons 1 which are expelled from the respective carriers 3 are advanced to a further station at which the upper ends 9a of the respective tubes or wrappers 9 are closed or closed and sealed in a manner well known in the art, e.g., in the art of closing the tops of containers for milk, juices or other beverages or in a manner known as twist top closing. FIG. 1 merely shows a top sealing drum 15 which attracts the tubes 9 by suction and supports or advances with or along suitable folding and closing or folding and sealing devices (not specifically shown in FIG. 1) so that each tampon 1 and the corresponding coiled string 13c are adequately confined in the respective tube 9. The thus confined tampons 1 thereupon advance along their second path (starting at the transfer drum 12) past a combined inspection and transfer drum 16, a further transfer drum 17, and toward and beyond a combined transfer and ejection drum 18 which is located at a last portion K of the path for the tampons 1. The drum 18 is preferably designed and positioned to change the orientation of the confined tampons 1 and their tubes 9 from vertical to horizontal for convenient introduction into cartons or other receptacles. For example, each such receptacle can confine an array containing a predetermined number of suitably distributed wrapped tampons 1.

The drums 16, 17 and 18 preferably attract the tampons 1 (i.e., the respective tubes 9) by suction.

The distance between the drums 11f and 12 is or can be selected with a view to ensure adequate cooling of the tubes 9 as well as adequate setting of the bonds between the at least partially overlapping panels 9d forming part of the closed and sealed ends 9c of the tubes 9.

It is clear that the apparatus of FIG. 1 can be provided with another endless chain or belt with suitable carriers serving to advance the tampons and their wrappers from the drum 11f to the transfer and ejection drum 18 or from the transfer drum 12 to the drum 18.

An important advantage of the improved method and apparatus is that the dimensions and configuration of each of a short or long series of closed and sealed ends 9c can exactly match a desirable optimum dimension and a desirable optimum configuration. This not only enhances the appearance of the wrapped tampons but also facilitates the task of collating selected numbers of tampons into arrays for introduction into cardboard boxes or other types of receptacles.

Another important advantage of the improved method and apparatus is that the closed and sealed ends 9c of the tubes 9 are highly unlikely to cause discomfort to the user of a tampon during separation of the tube 9.

An additional advantage of the improved method and apparatus is that the closed ends 9c of the tubes or envelopes 9 can be sealed in a highly reliable fashion. This reduces and practically eliminates the likelihood of contamination of a wrapped tampon.

The improved method and apparatus can be modified in a number of additional ways without departing from the spirit of the invention. For example, the material of the blanks 7 (i.e., the material of the tubes 9) can be selected in such a way that the overlapping portions of panels 9d forming the closed ends 9c can be reliably sealed in response to the application of pressure or in response to the application of heat and pressure. Furthermore, the exact construction and mode of operation of various constituents of the apparatus of FIG. 1 can be modified as desired or necessary, as long as they can carry out the aforedescribed operations in connection with the advancement of tampons and their receptacles, introduction of tampons into the receptacles, making and closing and sealing of the tubes, optimal shaping of the closed ends of the tubes, and closing and sealing of those ends of the tubes which are adjacent the leading ends of the respective tampons.

The novel feature of curling or coiling the strings 13 in the respective carriers 3 in response to downward movement of the tampons can be utilized in heretofore known apparatus for wrapping digital tampons. This renders it unnecessary to establish air flows which are to coil the strings in a manner as known from conventional tampon wrapping apparatus.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art and, therefore, such adaptations should and are intended to be comprehended within the meaning and range of equivalence of the appended claims.

What is claimed is:

1. A method of confining an elongated substantially cylindrical tampon, comprising the steps of introducing the tampon into a tubular carrier; surrounding at least a portion of the carrier by a blank of flexible sheet material and converting the blank into a tube having a first open end remote from and a second open end extending beyond an open end of the carrier; closing the second end of the tube including providing the second end with a plurality of at least partially overlapping panels which are disposed at least close to a plane at least substantially normal to a longitudinal axis of the carrier and which define at least one corner portion projecting substantially radially of and away from said axis and beyond an external surface of a portion of the tube adjacent said plane; and deforming the closed end of the tube including at least reducing the extent to which the at least one corner portion projects beyond said external surface.

2. The method of claim 1 of confining the tampon in a tube the sheet material of which is deformable in response to the application of heat, wherein said deforming step includes heating the closed end of the tube.

3. The method of claim 1, wherein said deforming step includes providing an outer surface of the closed end of the tube with a recess.

4. The method of claim 1, further comprising the step of expelling the tampon through the open end of the carrier with attendant separation of the tube from the carrier as a result of impingement of the tampon upon the closed and deformed end of the tube.

5. The method of claim 4, further comprising the step of closing the first end of the tube upon completion of said expelling step.

6. The method of claim 4, wherein said expelling step includes advancing in the carrier a pusher against the tampon and in a direction to move the tampon through and beyond the open end of the carrier.

7. The method of claim 1, further comprising the step of advancing the carrier substantially at right angles to said axis in the course of at least one of said introducing, surrounding, closing and deforming steps.

8. The method of claim 1, wherein said introducing step includes positioning the tampon in the carrier at a location at least slightly spaced apart from the open end of the carrier, and further comprising the step of shifting the tampon relative to the carrier toward the closed end of the tube not later than in the course of said deforming step.

9. The method of claim 1, wherein the sheet material of the tube is selected from the group consisting of cellophane and polypropylene.

10. The method of claim 1 of confining a tampon which is provided with an elongated string having a first end carried by the tampon and a second end, further comprising the step of maintaining the carrier in an at least substantially upright position so that the open end of the carrier is located below another end thereof, said introducing step including causing the string and thereupon the tampon to enter the carrier through the other end of the carrier so that the string depends from the tampon under the action of gravity, and further comprising the step of shifting the tampon in the carrier toward the closed end of the tube prior to said deforming step whereby the string curls above and along the closed end of the tube adjacent the open end of the carrier.

11. The method of claim 10, wherein said deforming step includes displacing a substantially central portion of the closed end of the tube toward the tampon in the carrier so that the displaced central portion is at least partially surrounded by the coiled string.

12. A method of confining an elongated substantially cylindrical tampon, comprising the steps of introducing the tampon into a tubular carrier; surrounding at least a portion of the carrier by a blank of flexible sheet material and converting the blank into a tube having a first open end remote from and a second open end extending beyond an open end of the carrier; closing the second end of the tube including providing the second end with a plurality of at least partially overlapping panels disposed at least close to a plane which is at least substantially normal to a longitudinal axis of the carrier; and deforming the closed end of the tube including providing an outer surface of the closed end with a recess.

13. The method of claim 12, wherein said deforming step further includes imparting an at least substantially circular shape to a portion of the closed end surrounding said recess.

14. Apparatus for confining elongated substantially cylindrical tampons, comprising means for advancing a series of successive tubular carriers along a predetermined path; means for introducing tampons into successive carriers in a first portion of said path; means for draping blanks of flexible sheet material around successive carriers in a second portion of said path, including means for converting the blanks into tubes each having a first open end remote from and a second open end extending beyond an open end of the respective carrier; means for closing the second ends of tubes surrounding the respective carriers in a third portion of said path, including means for providing each closed end with a plurality of at least partially overlapping panels each of which is disposed at least close to a plane at least substantially perpendicular to a longitudinal axis of the respective carrier and which define at least one corner portion projecting substantially radially of and away from the respective axis and beyond an external surface of a portion of the tube adjacent said plane; and means for deforming the closed ends of tubes surrounding successive carriers in a fourth portion of said path, including means for at least reducing the extent to which the corner portions of closed ends of tubes surrounding the respective carriers project beyond the respective external surfaces.

15. The apparatus of claim 14, further comprising means for expelling the tampons from successive carriers in a fifth portion of said path, including means for displacing the tampons through and beyond the open ends of the respective carriers so that the tampons strip the corresponding tubes off their carriers.

16. The apparatus of claim 14 for confining tampons in tubes the sheet material of which is deformable in response to the application of heat, wherein said deforming means includes profiled heating means arranged to contact the closed ends of tubes surrounding the respective carriers in said fourth portion of said path.

17. The apparatus of claim 16, wherein said profiled heating means includes at least one tool having a surface confronting the closed end of a tube in said fourth portion of said path, and means for effecting a movement of at least one of said at least one tool and a tube in said fourth portion of said path so as to effect an exchange of heat between the surface of the at least one tool and the confronting closed end.

18. The apparatus of claim 17, wherein said surface of said at least one tool has a protuberance and a recess surrounding said protuberance.

19. The apparatus of claim 17, wherein said surface of said at least one tool has a protuberance engageable with a central portion of the confronting closed end of a tube in said fourth portion of said path.

20. The apparatus of claim 14 for confining tampons which are provided with elongated strings each having a first end carried by the respective tampon and a second end, wherein said advancing means includes means for maintaining each carrier in an at least substantially upright position so that an open second end of each carrier is located below the tampon for the respective carrier, said introducing means including means for causing each string and thereupon the corresponding tampon to enter through the second end of the respective carrier so that the string depends from the corresponding tampon by gravity, and further comprising means for shifting the tampons in the respective carriers downwardly toward the closed ends of the respective tubes not later than in said fourth portion of said path whereby the strings curl along the closed ends of the respective tubes adjacent the open ends of the corresponding carriers.

21. The apparatus of claim 20, wherein said deforming means includes means for displacing a substantially central portion of the closed end of a tube in said fourth portion of said path toward the one end of the respective tampon so that the displaced substantially central portion is at least partially surrounded by the respective coiled string.

22. The apparatus of claim 20, further comprising means for expelling the tampons from successive carriers in a fifth portion of said path, including means for displacing the tampons through and beyond the open ends of the respective carriers so that the tampons strip the corresponding tubes off their carriers.

23. The apparatus of claim 14, wherein said advancing means includes means for moving successive carriers of said series in a predetermined direction and said first portion of said path is located upstream of said second portion.

24. The apparatus of claim 14, further comprising means for expelling the tampons from successive carriers from a fifth portion of said path into a second path, including means for displacing the tampons through and beyond the open ends of the respective carriers so that the tampons strip the corresponding tubes off their carriers, and means for closing the first open ends of the tubes in said second path.

25. Apparatus for confining elongated substantially cylindrical tampons, comprising means for advancing a series of successive tubular carriers along a predetermined path; means for introducing tampons into successive carriers in a first portion of said path; means for draping blanks of flexible sheet material around successive carriers in a second portion of said path, including means for converting the blanks into tubes each having a first open end remote from and a second open end extending beyond an open end of the respective carrier; means for closing the open ends of the tubes surrounding the respective carriers in a third portion of said path, including means for providing each closed end with a plurality of at least partially overlapping panels disposed at least close to a plane which is at least substantially perpendicular to a longitudinal axis of the respective carrier; and means for deforming the closed ends of the tubes surrounding the respective carriers in a fourth portion of said path, including means for providing an outer surface of each closed end with a recess.

26. The apparatus of claim 25, wherein said deforming means further includes means for imparting an at least substantially circular shape to a portion of each closed end surrounding the respective recess.

\* \* \* \* \*